(12) United States Patent
Cunningham et al.

(10) Patent No.: US 8,162,937 B2
(45) Date of Patent: Apr. 24, 2012

(54) HIGH VOLUME FLUID SEAL FOR ELECTROSURGICAL HANDPIECE

(75) Inventors: James S. Cunningham, Boulder, CO (US); Paul R. Romero, Loveland, CO (US); Jeffrey M. Roy, Boulder, CO (US)

(73) Assignee: Tyco Healthcare Group LP, Mansfield, MA (US)

( * ) Notice: Subject to any disclaimer, the term of this patent is extended or adjusted under 35 U.S.C. 154(b) by 971 days.

(21) Appl. No.: 12/163,134

(22) Filed: Jun. 27, 2008

(65) Prior Publication Data

US 2009/0322034 A1    Dec. 31, 2009

(51) Int. Cl.
*A61B 18/18*    (2006.01)
*A61B 18/04*    (2006.01)

(52) U.S. Cl. .............. 606/42; 606/31; 606/32; 606/41
(58) Field of Classification Search .............. 606/20–52, 606/41, 42
See application file for complete search history.

(56) References Cited

U.S. PATENT DOCUMENTS

| | | |
|---|---|---|
| 2,031,682 A | 2/1936 | Charles et al. |
| 2,102,270 A | 12/1937 | Hyams |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |
| 3,902,494 A | 9/1975 | Haberlen et al. |
| 3,906,955 A | 9/1975 | Roberts |
| 3,911,241 A | 10/1975 | Jarrard |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |

(Continued)

FOREIGN PATENT DOCUMENTS

DE    24 29 021 A1    1/1976

(Continued)

OTHER PUBLICATIONS

International Search Report from PCT-US03-37111; Jul. 21, 2004.

(Continued)

*Primary Examiner* — Nicholas D Lucchesi
*Assistant Examiner* — Leah Stohr (57) ABSTRACT

A fluid resistant seal connector for an electrosurgical handpiece includes a housing adapted to be supported within an electrosurgical handpiece. The housing includes opposing half sections each having an inner peripheral surface. The fluid resistant seal further includes a first seal adapted to engage an activation circuit of the handpiece and at least one second seal adapted to engage an electrosurgical supply wire in a fluid-tight relationship therewith. At least one of the first and second seals is configured to complement the inner peripheral surface of the housing.

20 Claims, 6 Drawing Sheets

U.S. PATENT DOCUMENTS

| | | | |
|---|---|---|---|
| 4,112,950 A | 9/1978 | Pike | |
| D253,247 S | 10/1979 | Gill | |
| 4,232,676 A | 11/1980 | Herczog | |
| 4,314,559 A | 2/1982 | Allen | |
| 4,427,006 A | 1/1984 | Nottke | |
| 4,443,935 A * | 4/1984 | Zamba et al. | 29/622 |
| 4,459,443 A | 7/1984 | Lewandowski | |
| 4,463,234 A | 7/1984 | Bennewitz | |
| 4,463,759 A | 8/1984 | Garito et al. | |
| 4,492,231 A | 1/1985 | Auth | |
| 4,492,832 A | 1/1985 | Taylor | |
| 4,545,375 A | 10/1985 | Cline | |
| 4,562,838 A | 1/1986 | Walker | |
| 4,589,411 A | 5/1986 | Friedman | |
| 4,593,691 A | 6/1986 | Lindstrom et al. | |
| 4,595,809 A | 6/1986 | Pool | |
| 4,606,342 A | 8/1986 | Zamba et al. | |
| 4,619,258 A | 10/1986 | Pool | |
| 4,620,548 A | 11/1986 | Hasselbrack | |
| 4,625,723 A | 12/1986 | Altnether et al. | |
| 4,640,279 A | 2/1987 | Beard | |
| 4,642,128 A | 2/1987 | Solorzano | |
| 4,655,215 A | 4/1987 | Pike | |
| 4,657,016 A | 4/1987 | Garito et al. | |
| 4,683,884 A | 8/1987 | Hatfield et al. | |
| 4,688,569 A | 8/1987 | Rabinowitz | |
| 4,701,193 A | 10/1987 | Robertson et al. | |
| 4,712,544 A | 12/1987 | Ensslin | |
| 4,735,603 A | 4/1988 | Goodson et al. | |
| 4,754,754 A | 7/1988 | Garito et al. | |
| 4,785,807 A | 11/1988 | Blanch | |
| 4,788,977 A | 12/1988 | Farin et al. | |
| 4,794,215 A | 12/1988 | Sawada et al. | |
| 4,796,623 A | 1/1989 | Krasner et al. | |
| 4,803,323 A | 2/1989 | Bauer et al. | |
| 4,811,733 A | 3/1989 | Borsanyi et al. | |
| 4,827,911 A | 5/1989 | Broadwin et al. | |
| 4,827,927 A | 5/1989 | Newton | |
| D301,739 S | 6/1989 | Turner et al. | |
| 4,846,790 A | 7/1989 | Hornlein et al. | |
| 4,850,353 A | 7/1989 | Stasz et al. | |
| 4,860,745 A | 8/1989 | Farin et al. | |
| 4,862,889 A | 9/1989 | Feucht | |
| 4,862,890 A | 9/1989 | Stasz et al. | |
| 4,869,715 A | 9/1989 | Sherburne | |
| 4,872,454 A | 10/1989 | DeOliveira et al. | |
| 4,876,110 A | 10/1989 | Blanch | |
| 4,886,060 A | 12/1989 | Wiksell | |
| 4,901,719 A | 2/1990 | Trenconsky et al. | |
| 4,903,696 A | 2/1990 | Stasz et al. | |
| 4,909,249 A | 3/1990 | Akkas et al. | |
| 4,911,159 A | 3/1990 | Johnson et al. | |
| 4,916,275 A | 4/1990 | Almond | |
| 4,919,129 A | 4/1990 | Weber, Jr. et al. | |
| 4,921,476 A | 5/1990 | Wuchinich | |
| 4,922,903 A | 5/1990 | Welch et al. | |
| 4,931,047 A | 6/1990 | Broadwin et al. | |
| 4,949,734 A | 8/1990 | Bernstein | |
| 4,969,885 A | 11/1990 | Farin | |
| 4,986,839 A | 1/1991 | Wertz et al. | |
| 4,988,334 A | 1/1991 | Hornlein et al. | |
| 5,000,754 A | 3/1991 | DeOliveira et al. | |
| 5,011,483 A | 4/1991 | Sleister | |
| 5,013,312 A | 5/1991 | Parins et al. | |
| 5,015,227 A | 5/1991 | Broadwin et al. | |
| 5,026,368 A | 6/1991 | Adair | |
| 5,035,695 A | 7/1991 | Weber, Jr. et al. | |
| 5,035,696 A | 7/1991 | Rydell | |
| 5,046,506 A | 9/1991 | Singer | |
| 5,055,100 A | 10/1991 | Olsen | |
| 5,071,418 A | 12/1991 | Rosenbaum | |
| 5,074,863 A | 12/1991 | Dines | |
| 5,076,276 A | 12/1991 | Sakurai et al. | |
| 5,088,997 A | 2/1992 | Delahuerga et al. | |
| 5,098,430 A | 3/1992 | Fleenor | |
| 5,100,402 A | 3/1992 | Fan | |
| 5,108,391 A | 4/1992 | Flachenecker et al. | |
| 5,133,714 A | 7/1992 | Beane | |
| 5,147,292 A | 9/1992 | Kullas et al. | |
| D330,253 S | 10/1992 | Burek | |
| 5,154,709 A | 10/1992 | Johnson | |
| 5,160,334 A | 11/1992 | Billings et al. | |
| 5,162,044 A | 11/1992 | Gahn et al. | |
| 5,167,659 A | 12/1992 | Ohtomo et al. | |
| 5,178,012 A | 1/1993 | Culp | |
| 5,178,605 A | 1/1993 | Imonti | |
| 5,190,517 A | 3/1993 | Zieve et al. | |
| 5,192,267 A | 3/1993 | Shapira et al. | |
| 5,195,959 A | 3/1993 | Smith | |
| 5,196,007 A | 3/1993 | Ellman et al. | |
| 5,197,962 A | 3/1993 | Sansom et al. | |
| 5,199,944 A | 4/1993 | Cosmescu | |
| 5,217,457 A | 6/1993 | Delahuerga et al. | |
| 5,224,944 A | 7/1993 | Elliott | |
| 5,226,904 A | 7/1993 | Gentelia et al. | |
| 5,233,515 A | 8/1993 | Cosman | |
| 5,234,428 A | 8/1993 | Kaufman | |
| 5,234,429 A | 8/1993 | Goldhaber | |
| 5,242,442 A | 9/1993 | Hirschfeld | |
| 5,244,462 A | 9/1993 | Delahuerga et al. | |
| 5,246,440 A | 9/1993 | Van Noord | |
| 5,254,082 A | 10/1993 | Takase | |
| 5,254,117 A | 10/1993 | Rigby et al. | |
| 5,256,138 A | 10/1993 | Burek et al. | |
| 5,261,906 A | 11/1993 | Pennino et al. | |
| 5,269,781 A | 12/1993 | Hewell, III | |
| 5,300,087 A | 4/1994 | Knoepfler | |
| 5,304,763 A | 4/1994 | Ellman et al. | |
| 5,306,238 A | 4/1994 | Fleenor | |
| 5,312,329 A | 5/1994 | Beaty et al. | |
| 5,312,400 A | 5/1994 | Bales et al. | |
| 5,312,401 A | 5/1994 | Newton et al. | |
| 5,318,516 A | 6/1994 | Cosmescu | |
| 5,318,565 A | 6/1994 | Kuriloff et al. | |
| 5,322,503 A | 6/1994 | Desai | |
| 5,330,470 A | 7/1994 | Hagen | |
| 5,334,183 A | 8/1994 | Wuchinich | |
| 5,342,356 A | 8/1994 | Ellman et al. | |
| 5,348,555 A | 9/1994 | Zinnanti | |
| 5,366,464 A | 11/1994 | Belknap | |
| 5,376,089 A * | 12/1994 | Smith | 606/42 |
| 5,380,320 A | 1/1995 | Morris | |
| 5,382,247 A | 1/1995 | Cimino et al. | |
| 5,395,363 A | 3/1995 | Billings et al. | |
| 5,399,823 A | 3/1995 | McCusker | |
| 5,401,273 A | 3/1995 | Shippert | |
| 5,403,882 A | 4/1995 | Huggins | |
| 5,406,945 A | 4/1995 | Riazzi et al. | |
| 5,409,484 A | 4/1995 | Erlich et al. | |
| 5,413,575 A | 5/1995 | Haenggi | |
| 5,421,829 A | 6/1995 | Olichney et al. | |
| 5,423,838 A | 6/1995 | Willard | |
| 5,431,645 A | 7/1995 | Smith et al. | |
| 5,431,650 A | 7/1995 | Cosmescu | |
| 5,451,222 A | 9/1995 | De Maagd et al. | |
| 5,460,602 A | 10/1995 | Shapira | |
| 5,462,522 A | 10/1995 | Sakurai et al. | |
| 5,468,240 A | 11/1995 | Gentelia et al. | |
| 5,472,442 A | 12/1995 | Klicek | |
| 5,472,443 A | 12/1995 | Cordis et al. | |
| 5,484,398 A | 1/1996 | Stoddard | |
| 5,484,434 A | 1/1996 | Cartmell et al. | |
| 5,486,162 A | 1/1996 | Brumbach | |
| 5,496,314 A | 3/1996 | Eggers | |
| 5,498,654 A | 3/1996 | Shimasaki et al. | |
| D370,731 S | 6/1996 | Corace et al. | |
| 5,531,722 A | 7/1996 | Van Hale | |
| 5,549,604 A | 8/1996 | Sutcu et al. | |
| 5,561,278 A | 10/1996 | Rutten | |
| 5,601,224 A | 2/1997 | Bishop et al. | |
| 5,609,573 A | 3/1997 | Sandock | |
| 5,626,575 A | 5/1997 | Crenner | |
| 5,630,417 A | 5/1997 | Petersen et al. | |
| 5,630,426 A | 5/1997 | Eggers et al. | |
| 5,630,812 A | 5/1997 | Ellman et al. | |
| 5,633,578 A | 5/1997 | Eggers et al. | |
| 5,634,912 A | 6/1997 | Injev | |

| | | | | | | |
|---|---|---|---|---|---|---|
| 5,634,935 | A | 6/1997 | Taheri | 6,258,088 | B1 | 7/2001 | Tzonev et al. |
| 5,643,256 | A | 7/1997 | Urueta | 6,273,862 | B1 | 8/2001 | Privitera et al. |
| D384,148 | S | 9/1997 | Monson | 6,277,083 | B1 | 8/2001 | Eggers et al. |
| 5,669,907 | A | 9/1997 | Platt, Jr. et al. | 6,286,512 | B1 | 9/2001 | Loeb et al. |
| 5,674,219 | A | 10/1997 | Monson et al. | 6,287,305 | B1 | 9/2001 | Heim et al. |
| 5,693,044 | A | 12/1997 | Cosmescu | 6,287,344 | B1 | 9/2001 | Wampler et al. |
| 5,693,050 | A | 12/1997 | Speiser | 6,312,441 | B1 | 11/2001 | Deng |
| 5,693,052 | A | 12/1997 | Weaver | 6,325,799 | B1 | 12/2001 | Goble |
| 5,697,926 | A | 12/1997 | Weaver | D453,222 | S | 1/2002 | Garito et al. |
| 5,702,360 | A | 12/1997 | Dieras et al. | D453,833 | S | 2/2002 | Hess |
| 5,702,387 | A | 12/1997 | Arts et al. | 6,350,276 | B1 | 2/2002 | Knowlton |
| 5,712,543 | A | 1/1998 | Sjostrom | 6,352,544 | B1 | 3/2002 | Spitz |
| 5,713,895 | A | 2/1998 | Lontine et al. | 6,355,034 | B2 | 3/2002 | Cosmescu |
| 5,720,745 | A | 2/1998 | Farin et al. | 6,358,281 | B1 | 3/2002 | Berrang et al. |
| D393,067 | S | 3/1998 | Geary et al. | 6,361,532 | B1 | 3/2002 | Burek |
| 5,749,869 | A | 5/1998 | Lindenmeier et al. | D457,955 | S | 5/2002 | Bilitz |
| 5,765,418 | A | 6/1998 | Rosenberg | 6,386,032 | B1 | 5/2002 | Lemkin et al. |
| 5,776,092 | A | 7/1998 | Farin et al. | 6,395,001 | B1 | 5/2002 | Ellman et al. |
| 5,788,688 | A | 8/1998 | Bauer et al. | 6,402,741 | B1 | 6/2002 | Keppel et al. |
| 5,797,907 | A | 8/1998 | Clement | 6,402,742 | B1 | 6/2002 | Blewett et al. |
| 5,800,431 | A | 9/1998 | Brown | 6,402,743 | B1 | 6/2002 | Orszulak et al. |
| 5,836,897 | A | 11/1998 | Sakurai et al. | 6,402,748 | B1 | 6/2002 | Schoenman et al. |
| 5,836,909 | A | 11/1998 | Cosmescu | 6,409,725 | B1 | 6/2002 | Khandkar et al. |
| 5,836,944 | A | 11/1998 | Cosmescu | 6,413,255 | B1 | 7/2002 | Stern |
| D402,030 | S | 12/1998 | Roberts et al. | 6,416,491 | B1 | 7/2002 | Edwards et al. |
| D402,031 | S | 12/1998 | Roberts et al. | 6,416,509 | B1 | 7/2002 | Goble et al. |
| 5,843,109 | A | 12/1998 | Mehta et al. | 6,425,912 | B1 | 7/2002 | Knowlton |
| 5,846,236 | A | 12/1998 | Lindenmeier et al. | 6,458,122 | B1 | 10/2002 | Pozzato |
| 5,859,527 | A | 1/1999 | Cook | 6,458,125 | B1 | 10/2002 | Cosmescu |
| 5,868,768 | A | 2/1999 | Wicherski et al. | 6,461,352 | B2 | 10/2002 | Morgan et al. |
| 5,876,400 | A | 3/1999 | Songer | 6,464,702 | B2 | 10/2002 | Schulze et al. |
| 5,888,200 | A | 3/1999 | Walen | 6,471,659 | B2 | 10/2002 | Eggers et al. |
| 5,893,848 | A | 4/1999 | Negus et al. | 6,494,882 | B1 | 12/2002 | Lebouitz et al. |
| 5,893,849 | A | 4/1999 | Weaver | 6,500,169 | B1 | 12/2002 | Deng |
| 5,893,862 | A | 4/1999 | Pratt et al. | 6,511,479 | B2 | 1/2003 | Gentelia et al. |
| 5,913,864 | A | 6/1999 | Garito et al. | 6,526,320 | B2 | 2/2003 | Mitchell |
| 5,919,219 | A | 7/1999 | Knowlton | 6,551,313 | B1 | 4/2003 | Levin |
| 5,928,159 | A | 7/1999 | Eggers et al. | 6,558,383 | B2 | 5/2003 | Cunningham et al. |
| 5,938,589 | A | 8/1999 | Wako et al. | 6,585,664 | B2 | 7/2003 | Burdorff et al. |
| 5,941,887 | A | 8/1999 | Steen et al. | 6,589,239 | B2 | 7/2003 | Khandkar et al. |
| 5,944,737 | A | 8/1999 | Tsonton et al. | 6,610,054 | B1 | 8/2003 | Edwards et al. |
| 5,951,548 | A | 9/1999 | DeSisto et al. | 6,610,057 | B1 | 8/2003 | Ellman et al. |
| 5,951,581 | A | 9/1999 | Saadat et al. | 6,616,658 | B2 | 9/2003 | Ineson |
| 5,954,686 | A | 9/1999 | Garito et al. | 6,618,626 | B2 | 9/2003 | West, Jr. et al. |
| 5,972,007 | A | 10/1999 | Sheffield et al. | 6,620,161 | B2 | 9/2003 | Schulze et al. |
| 6,004,318 | A | 12/1999 | Garito et al. | 6,632,193 | B1 | 10/2003 | Davison et al. |
| 6,004,333 | A | 12/1999 | Sheffield et al. | 6,652,514 | B2 | 11/2003 | Ellman et al. |
| 6,004,335 | A | 12/1999 | Vaitekunas et al. | 6,662,053 | B2 | 12/2003 | Borkan |
| 6,010,499 | A | 1/2000 | Cobb | 6,669,691 | B1 | 12/2003 | Taimisto |
| 6,022,347 | A | 2/2000 | Lindenmeier et al. | 6,685,701 | B2 | 2/2004 | Orszulak et al. |
| 6,045,564 | A | 4/2000 | Walen | 6,685,704 | B2 | 2/2004 | Greep |
| 6,063,050 | A | 5/2000 | Manna et al. | 6,702,812 | B2 | 3/2004 | Cosmescu |
| 6,068,603 | A | 5/2000 | Suzuki | 6,710,546 | B2 | 3/2004 | Crenshaw |
| 6,068,627 | A | 5/2000 | Orszulak et al. | 6,712,813 | B2 | 3/2004 | Ellman et al. |
| 6,070,444 | A | 6/2000 | Lontine et al. | 6,719,746 | B2 | 4/2004 | Blanco |
| 6,071,281 | A | 6/2000 | Burnside et al. | 6,740,079 | B1 | 5/2004 | Eggers et al. |
| 6,074,386 | A | 6/2000 | Goble et al. | 6,747,218 | B2 | 6/2004 | Huseman et al. |
| 6,074,387 | A | 6/2000 | Heim et al. | D493,530 | S | 7/2004 | Reschke |
| 6,086,544 | A | 7/2000 | Hibner et al. | D493,888 | S | 8/2004 | Reschke |
| 6,090,123 | A | 7/2000 | Culp et al. | D494,270 | S | 8/2004 | Reschke |
| 6,099,525 | A | 8/2000 | Cosmescu | D495,051 | S | 8/2004 | Reschke |
| 6,117,134 | A | 9/2000 | Cunningham et al. | D495,052 | S | 8/2004 | Reschke |
| 6,139,547 | A | 10/2000 | Lontine et al. | 6,794,929 | B2 | 9/2004 | Pelly |
| D433,752 | S | 11/2000 | Saravia | 6,830,569 | B2 | 12/2004 | Thompson et al. |
| 6,142,995 | A | 11/2000 | Cosmescu | 6,840,948 | B2 | 1/2005 | Albrecht et al. |
| 6,146,353 | A | 11/2000 | Platt, Jr. | 6,855,140 | B2 | 2/2005 | Albrecht et al. |
| 6,149,648 | A | 11/2000 | Cosmescu | 6,902,536 | B2 | 6/2005 | Manna et al. |
| 6,156,035 | A | 12/2000 | Songer | 6,905,496 | B1 | 6/2005 | Ellman et al. |
| 6,197,024 | B1 | 3/2001 | Sullivan | 6,923,804 | B2 | 8/2005 | Eggers et al. |
| 6,200,311 | B1 | 3/2001 | Danek et al. | 6,923,809 | B2 | 8/2005 | Eggers et al. |
| D441,077 | S | 4/2001 | Garito et al. | 6,939,347 | B2 | 9/2005 | Thompson |
| 6,213,999 | B1 | 4/2001 | Platt, Jr. et al. | 6,955,674 | B2 | 10/2005 | Eick et al. |
| 6,214,003 | B1 | 4/2001 | Morgan et al. | D515,412 | S | 2/2006 | Waaler et al. |
| 6,238,388 | B1 | 5/2001 | Ellman et al. | 7,033,353 | B2 | 4/2006 | Stoddard et al. |
| 6,241,723 | B1 | 6/2001 | Heim et al. | D521,641 | S | 5/2006 | Reschke et al. |
| 6,241,753 | B1 | 6/2001 | Knowlton | D535,396 | S | 1/2007 | Reschke et al. |
| 6,249,706 | B1 | 6/2001 | Sobota et al. | 7,156,842 | B2 | 1/2007 | Sartor et al. |
| 6,251,110 | B1 | 6/2001 | Wampler | 7,156,844 | B2 | 1/2007 | Reschke et al. |
| 6,257,241 | B1 | 7/2001 | Wampler | 7,235,072 | B2 | 6/2007 | Sartor et al. |

| | | | |
|---|---|---|---|
| 7,241,294 B2 | 7/2007 | Reschke | |
| 7,244,257 B2 | 7/2007 | Podhajsky et al. | |
| 7,311,706 B2 | 12/2007 | Schoenman et al. | |
| 7,393,354 B2 | 7/2008 | Buchman, II et al. | |
| 2001/0047183 A1 | 11/2001 | Privitera et al. | |
| 2001/0049524 A1 | 12/2001 | Morgan et al. | |
| 2002/0019596 A1 | 2/2002 | Eggers et al. | |
| 2002/0019631 A1 | 2/2002 | Kidder et al. | |
| 2002/0022838 A1 | 2/2002 | Cunningham et al. | |
| 2002/0026145 A1 | 2/2002 | Bagaoisan et al. | |
| 2002/0035364 A1 | 3/2002 | Schoenman et al. | |
| 2002/0049427 A1 | 4/2002 | Wiener et al. | |
| 2002/0058958 A1 | 5/2002 | Walen | |
| 2002/0087179 A1 | 7/2002 | Culp et al. | |
| 2002/0095199 A1 | 7/2002 | West, Jr. et al. | |
| 2002/0103485 A1 | 8/2002 | Melnyk et al. | |
| 2002/0111622 A1 | 8/2002 | Khandkar et al. | |
| 2002/0133148 A1 | 9/2002 | Daniel et al. | |
| 2002/0151886 A1 | 10/2002 | Wood | |
| 2002/0151887 A1 | 10/2002 | Stern et al. | |
| 2002/0156471 A1 | 10/2002 | Stern et al. | |
| 2002/0173776 A1 | 11/2002 | Batchelor et al. | |
| 2002/0198519 A1 | 12/2002 | Qin et al. | |
| 2003/0004508 A1 | 1/2003 | Morgan et al. | |
| 2003/0014043 A1 | 1/2003 | Henry et al. | |
| 2003/0032950 A1 | 2/2003 | Altshuler et al. | |
| 2003/0050633 A1 | 3/2003 | Ellman et al. | |
| 2003/0055421 A1 | 3/2003 | West et al. | |
| 2003/0061661 A1 | 4/2003 | Borders et al. | |
| 2003/0065321 A1 | 4/2003 | Carmel et al. | |
| 2003/0078572 A1 | 4/2003 | Pearson et al. | |
| 2003/0083655 A1 | 5/2003 | Van Wyk | |
| 2003/0088247 A1 | 5/2003 | Ineson | |
| 2003/0109864 A1 | 6/2003 | Greep et al. | |
| 2003/0109865 A1 | 6/2003 | Greep et al. | |
| 2003/0130663 A1 | 7/2003 | Walen | |
| 2003/0144680 A1 | 7/2003 | Kellogg et al. | |
| 2003/0163125 A1 | 8/2003 | Greep | |
| 2003/0199856 A1 | 10/2003 | Hill et al. | |
| 2003/0199866 A1 | 10/2003 | Stern et al. | |
| 2003/0199869 A1 | 10/2003 | Johnson et al. | |
| 2003/0212393 A1 | 11/2003 | Knowlton et al. | |
| 2003/0212397 A1 | 11/2003 | Avrahami et al. | |
| 2003/0216728 A1 | 11/2003 | Stern et al. | |
| 2003/0220635 A1 | 11/2003 | Knowlton et al. | |
| 2003/0220638 A1 | 11/2003 | Metzger | |
| 2003/0225401 A1 | 12/2003 | Eggers et al. | |
| 2003/0229341 A1 | 12/2003 | Albrecht et al. | |
| 2003/0229343 A1 | 12/2003 | Albrecht et al. | |
| 2004/0000316 A1 | 1/2004 | Knowlton et al. | |
| 2004/0002704 A1 | 1/2004 | Knowlton et al. | |
| 2004/0002705 A1 | 1/2004 | Knowlton et al. | |
| 2004/0010246 A1 | 1/2004 | Takahashi | |
| 2004/0015160 A1 | 1/2004 | Lovewell | |
| 2004/0015161 A1 | 1/2004 | Lovewell | |
| 2004/0015162 A1 | 1/2004 | McGaffigan | |
| 2004/0015216 A1 | 1/2004 | DeSisto | |
| 2004/0024395 A1 | 2/2004 | Ellman et al. | |
| 2004/0024396 A1 | 2/2004 | Eggers | |
| 2004/0030328 A1 | 2/2004 | Eggers et al. | |
| 2004/0030330 A1 | 2/2004 | Brassell et al. | |
| 2004/0030332 A1 | 2/2004 | Knowlton et al. | |
| 2004/0030367 A1 | 2/2004 | Yamaki et al. | |
| 2004/0034346 A1 | 2/2004 | Stern et al. | |
| 2004/0054370 A1 | 3/2004 | Given | |
| 2004/0111087 A1 | 6/2004 | Stern et al. | |
| 2004/0124964 A1 | 7/2004 | Wang et al. | |
| 2004/0127889 A1 | 7/2004 | Zhang et al. | |
| 2004/0143677 A1 | 7/2004 | Novak | |
| 2004/0147909 A1 | 7/2004 | Johnston et al. | |
| 2004/0162553 A1 | 8/2004 | Peng et al. | |
| 2004/0167512 A1 | 8/2004 | Stoddard et al. | |
| 2004/0172011 A1 | 9/2004 | Wang et al. | |
| 2004/0172015 A1 | 9/2004 | Novak | |
| 2004/0172016 A1 | 9/2004 | Bek et al. | |
| 2004/0181140 A1 | 9/2004 | Falwell et al. | |
| 2004/0243120 A1 | 12/2004 | Orszulak et al. | |
| 2004/0267252 A1 | 12/2004 | Washington et al. | |
| 2004/0267254 A1 | 12/2004 | Manzo et al. | |
| 2004/0267297 A1 | 12/2004 | Malackowski | |
| 2005/0033286 A1 | 2/2005 | Eggers et al. | |
| 2005/0059858 A1 | 3/2005 | Frith et al. | |
| 2005/0059967 A1 | 3/2005 | Breazeale, Jr. et al. | |
| 2005/0065510 A1 | 3/2005 | Carmel et al. | |
| 2005/0070891 A1 | 3/2005 | DeSisto | |
| 2005/0085804 A1 | 4/2005 | McGaffigan | |
| 2005/0096645 A1 | 5/2005 | Wellman et al. | |
| 2005/0096646 A1 | 5/2005 | Wellman et al. | |
| 2005/0096681 A1 | 5/2005 | Desinger et al. | |
| 2005/0113817 A1 | 5/2005 | Isaacson et al. | |
| 2005/0113818 A1 | 5/2005 | Sartor et al. | |
| 2005/0113824 A1 | 5/2005 | Sartor et al. | |
| 2005/0113825 A1 | 5/2005 | Cosmescu | |
| 2005/0149001 A1 | 7/2005 | Uchikubo et al. | |
| 2005/0154385 A1 | 7/2005 | Heim et al. | |
| 2006/0041257 A1 | 2/2006 | Sartor et al. | |
| 2006/0058783 A1 | 3/2006 | Buchman | |
| 2006/0178667 A1 | 8/2006 | Sartor et al. | |
| 2007/0049926 A1 | 3/2007 | Sartor | |
| 2007/0093810 A1 | 4/2007 | Sartor | |
| 2007/0142832 A1 | 6/2007 | Sartor | |
| 2007/0260239 A1 | 11/2007 | Podhajsky et al. | |
| 2007/0260240 A1 | 11/2007 | Rusin | |

FOREIGN PATENT DOCUMENTS

| | | |
|---|---|---|
| DE | 24 60 481 A1 | 6/1976 |
| DE | 30 45 996 | 7/1982 |
| EP | 0186369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1 645 233 | 4/2006 |
| EP | 1656900 | 5/2006 |
| EP | 1645234 | 12/2006 |
| EP | 1852078 | 11/2007 |
| FR | 2235669 | 1/1975 |
| FR | 2798579 | 3/2001 |
| WO | WO 94/20032 | 9/1994 |
| WO | WO 96/39086 | 12/1996 |
| WO | WO 98/43264 | 10/1998 |
| WO | WO 01/64122 | 9/2001 |
| WO | WO 02/47568 A1 | 6/2002 |
| WO | WO 2004/010883 A1 | 2/2004 |
| WO | WO 2004/045436 A1 | 6/2004 |
| WO | WO 2004/073753 A2 | 9/2004 |
| WO | WO 2005/060849 A1 | 7/2005 |

OTHER PUBLICATIONS

International Search Report from PCT-US04-04685; Aug. 6, 2004.
International Search Report from EP-0401-5980; Sep. 30, 2004.
International Search Report from PCT-US03-22900; Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.
International Search Report from Application No. EP 06 00 6908 dated Feb. 25, 2009.
International Search Report from Application No. EP 08 02 1070 dated Apr. 1, 2009.
Zucker, Karl, Surgical Laparoscopy, Lippincott Williams & Wilkins, Ed. 2, 2001 (2 pages).

* cited by examiner

HIGH VOLUME FLUID SEAL FOR ELECTROSURGICAL HANDPIECE

BACKGROUND

1. Technical Field

The present disclosure relates generally to electrosurgical instruments and, more particularly, to an electrosurgical handpiece having a fluid resistant seal.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, that transfer radio-frequency (RF) electrical or electrosurgical energy to a tissue site. Typically, these electrosurgical devices introduce an RF cauterizing current, a cutting current, or a blend thereof to a conductive blade attached to a housing and activateable via one or more switches. In some instances, these devices include suction and irrigation capabilities. These features are typically controlled through control mechanisms contained within an actuator disposed on the housing or on a generator, attached to the electrosurgical instrument.

In some procedures, fluids and bio-materials collect near the device adjacent sensitive electronic and/or electro-mechanical areas, e.g., these fluids and bio-materials may deposit on the control mechanisms and wires within the housing thereby compromising electrical connections. Typically, manufacturers of electrosurgical devices utilize plastic overmolding to protect sensitive instrument areas and/or dielectric insulative protection around wires and electrical connections within the device. However, the overmolding process typically involves utilizing high pressures and high temperatures, both of which may compromise wiring insulation as well as shift wires causing electrical disconnections during manufacturing.

SUMMARY

According to one aspect of the present disclosure, a fluid resistant seal connector for an electrosurgical handpiece includes a housing supported within an electrosurgical handpiece. The housing includes opposing half sections each having an inner peripheral surface. The fluid resistant seal further includes a first seal that engages an activation circuit in a fluid-tight manner and one or more second seals that engage an electrosurgical supply wire in a fluid-tight relationship. The first and/or second seals are configured to complement the inner peripheral profile of the housing.

According to another aspect of the present disclosure, the fluid resistant seal connector includes a housing supported within an electrosurgical handpiece having opposing half sections each having an inner peripheral surface. The seal connector further includes a first seal that engages an activation circuit in fluid-tight relationship therewith and a second seal that engages an electrosurgical supply wire in a fluid-tight manner. The first and/or second seals are configured to complement the inner peripheral profile of the housing. One or more of seals include mutually engaging opposing sections that encapsulate and secure the respective activation circuit and supply wire upon assembly of the opposing half sections of the housing. The seal connector includes a plurality of support members disposed on the outer periphery of the housing configured to engage an inner surface of the electrosurgical handpiece. Upon assembly of the handpiece, the support members compress the housing to enhance the fluid-tight seal between the housing, activation circuit and support wire.

The present disclosure also provides a method of manufacturing a fluid seal connector for an electrosurgical handpiece. The method includes the initial step of providing a housing adapted to be supported within an electrosurgical handpiece. The housing includes opposing half sections each having an inner peripheral surface. The method also includes the step of providing a first seal and at least one second seal configured to complement the inner peripheral profile of the housing. The method further includes the steps of engaging the first seal with an activation circuit, engaging the second seal with an electrosurgical supply wire, and assembling the housing such that the first and second seals encapsulate the respective activation circuit and supply wire in a fluid-tight manner.

BRIEF DESCRIPTION OF THE DRAWINGS

Various embodiments of the subject instrument are described herein with reference to the drawings wherein.

DETAILED DESCRIPTION

Embodiments of the presently disclosed electrosurgical handpiece are described in detail with reference to the drawing figures wherein like reference numerals identify similar or identical elements. As used herein, the term "distal" refers to that portion which is further from the user while the term "proximal" refers to that portion which is closer to the user or surgeon.

Figure 1:
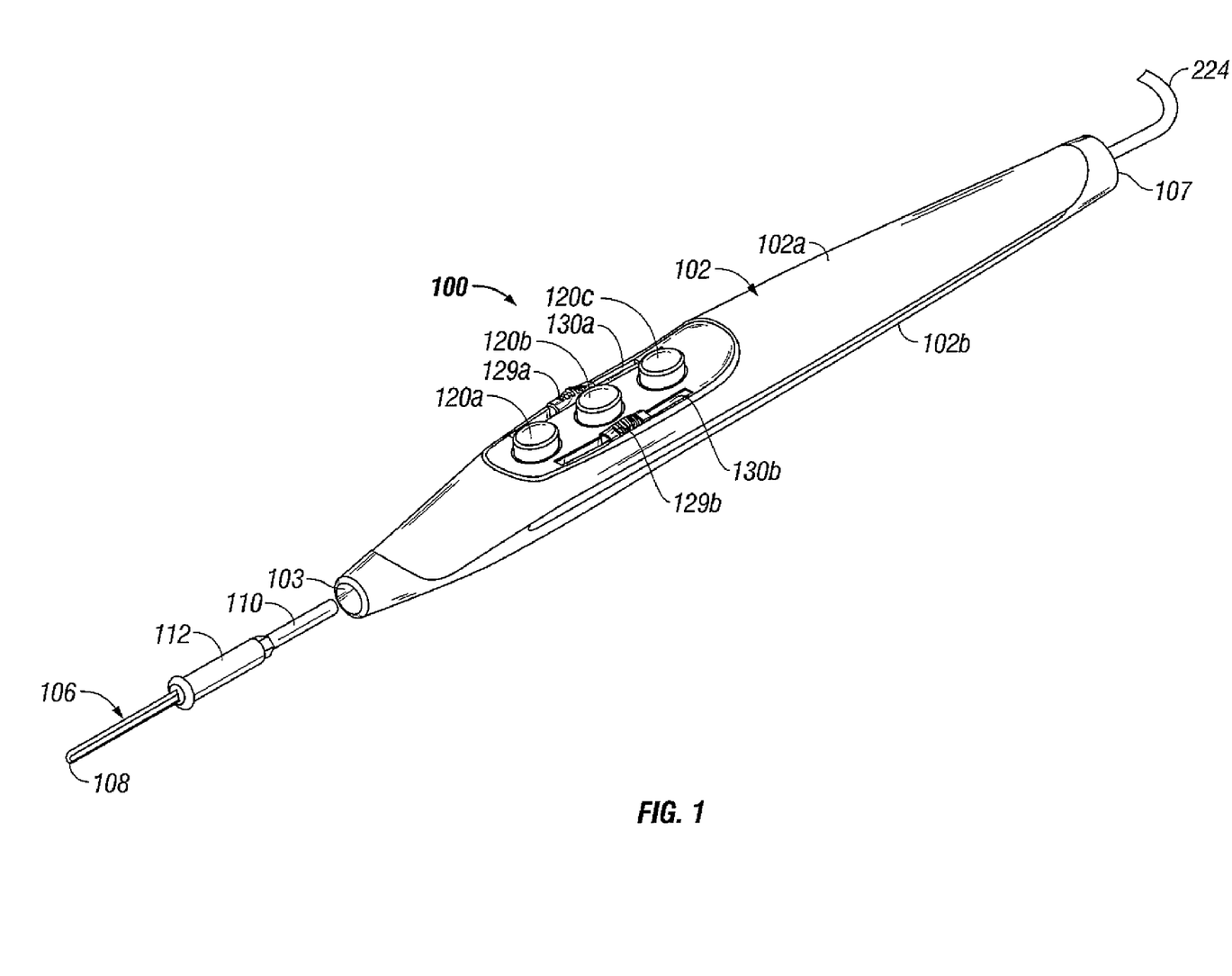
FIG. 1 is a perspective view of an electrosurgical handpiece in accordance with an embodiment of the present disclosure.

FIG. 1 sets forth a perspective view of an electrosurgical system including an electrosurgical pencil 100 constructed in accordance with one embodiment of the present disclosure. While the following description will be directed towards electrosurgical pencils it is envisioned that the features and concepts (or portions thereof) of the present disclosure can be applied to any electrosurgical type instrument, e.g., forceps, suction coagulators, vessel sealers, wands, etc.

Figure 2:
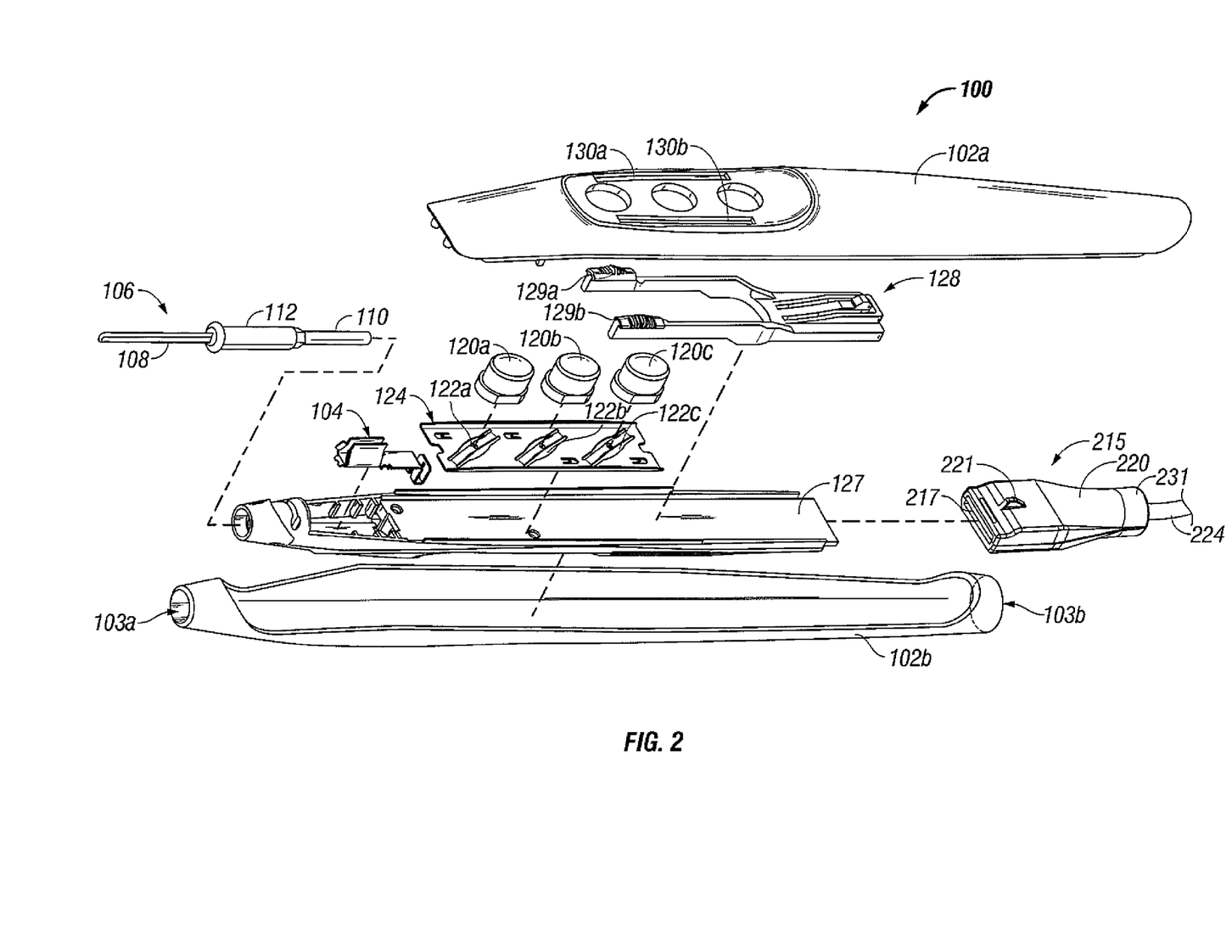
FIG. 2 is an exploded, perspective view of the electrosurgical handpiece of FIG. 1.

As seen in FIGS. 1 and 2, electrosurgical pencil 100 includes an elongated housing 102 having a top-half shell portion 102a and a bottom-half shell portion 102b. Top-half shell portion 102a and bottom-half shell portion 102b may be bonded together using methods known by those skilled in the art, e.g., sonic energy, adhesives, snap-fit assemblies, etc. Pencil 100 includes a distal opening 103a, through which an electrocautery blade 106 extends, and a proximal opening 103b, through which a connecting wire 224 extends adjacent proximal end 107 of housing 102. Electrosurgical pencil 100 is coupled to a source of electrosurgical energy, e.g., a generator (not shown) via the connecting wire 224.

Electrocautery blade 106 is supported in a collar 112 that is positioned between a distal end 108 and a proximal end 110 of electrocautery blade 106. Collar 112 has a shaped outer surface configured to complement the inner profile of distal opening 103a in a slide-fit or otherwise secure-fit manner.

Electrosurgical pencil 100 further includes a blade receptacle 104 (see FIG. 2) disposed at the distal end 103 of housing 102, and a replaceable electrocautery end effector 106 operatively and removably connectable to blade receptacle 104. Electrocautery end effector 106 may be in the form of a needle, loop, blade, wand or any shape known in the art. The distal end 108 of blade 106 extends beyond receptacle 104 while the proximal end 110 of blade 106 is selectively retained by receptacle 104 within the distal end 103 of housing 102. Blade receptacle 104 is electrically connected to voltage divider network 127 (FIG. 2) as explained in more detail below.

With reference to FIGS. 1 and 2, electrosurgical pencil 100 includes three activation switches 120a-120c, each of which extends through top-half shell portion 102a of housing 102. Each activation switch 120a-120c is operatively supported on a respective tactile element 122a-122c (here shown as a snap-dome switch) provided on a switch plate 124. Each activation switch 120a-120c controls the transmission of RF electrical energy supplied from the generator "G" to electrosurgical blade 106. More particularly, switch plate 124 is positioned on top of the voltage divider network 127 (hereinafter "VDN 127") such that tactile elements 122a-122c are operatively associated therewith. VDN 127 (e.g., here shown as a film-type potentiometer) forms a switch closure. As will be discussed in further detail below, a fluid resistive seal connector 215, configured to house an electrical connection between VDN 127 and connecting wire 224, is supported in housing 102 near proximal end 107.

Electrosurgical pencil 100 may also include an intensity controller 128 slidingly supported on or in housing 102. Intensity controller 128 includes a pair of nubs 129a, 129b which are slidingly supported, one each, in respective guide channels 130a, 130b, formed in top-half shell portion 102a of housing 102. Guide channels 130a, 130b are formed on either side of activations switches 120a-120c. In this manner, as intensity controller 128 is displaced in a distal and/or proximal direction relative to housing 102, the intensity of RF energy being transmitted to electrocautery end effector 106 varies accordingly.

With reference to FIGS. 2, 3 4A, and 4B, fluid resistive seal connector 215 is shown as part of the pencil assembly and includes a housing 220 having housing half sections 220a and 220b. Housing 220 also includes a distal slot 217 formed therein, configured to mechanically receive and interface with a proximal end of VDN 127. A proximal opening 230 (FIG. 4A) is also defined in housing 220 and is configured to mechanically receive and interface with the connecting wire 224. Proximal opening 230 may include a generally circular-shaped outer surface 231 configured to complement the inner profile of proximal opening 103b of housing 102 to assure secure engagement therewith during assembly.

Figure 3:
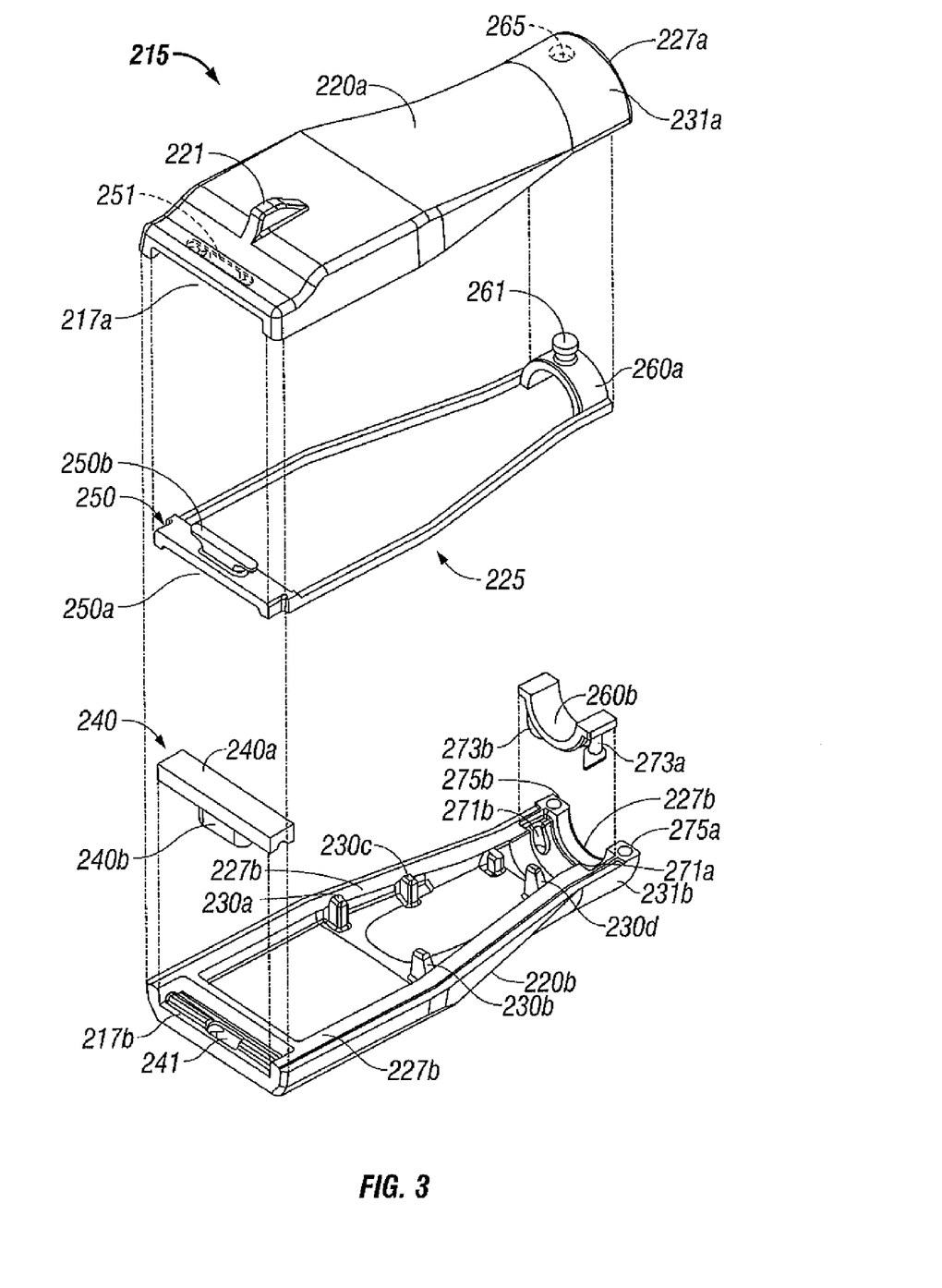
FIG. 3 is an exploded, perspective view of a fluid seal in accordance with one embodiment of the present disclosure.
Figure 4A:
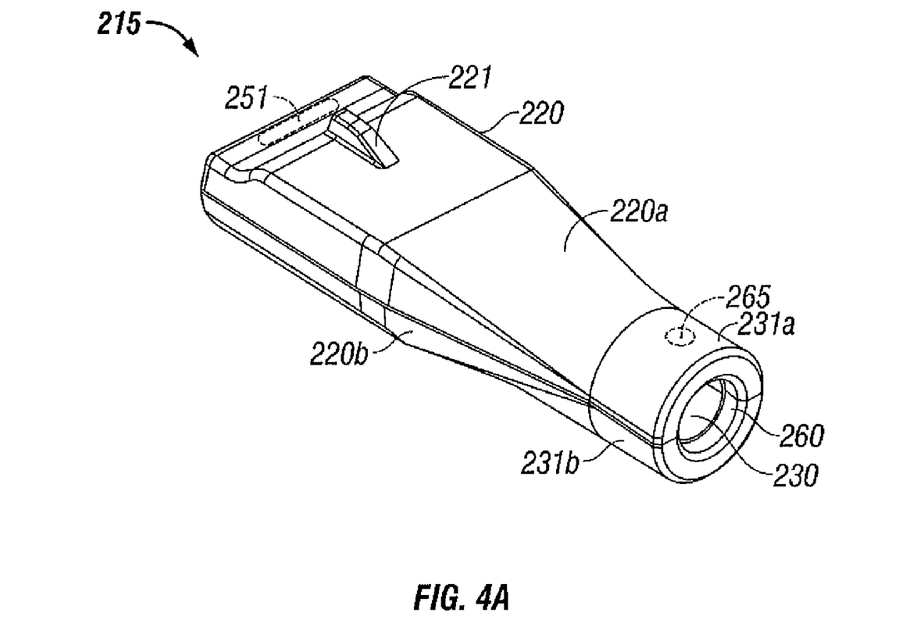
FIG. 4A is an assembled, top perspective view of the fluid seal of FIG. 3.
Figure 4B:
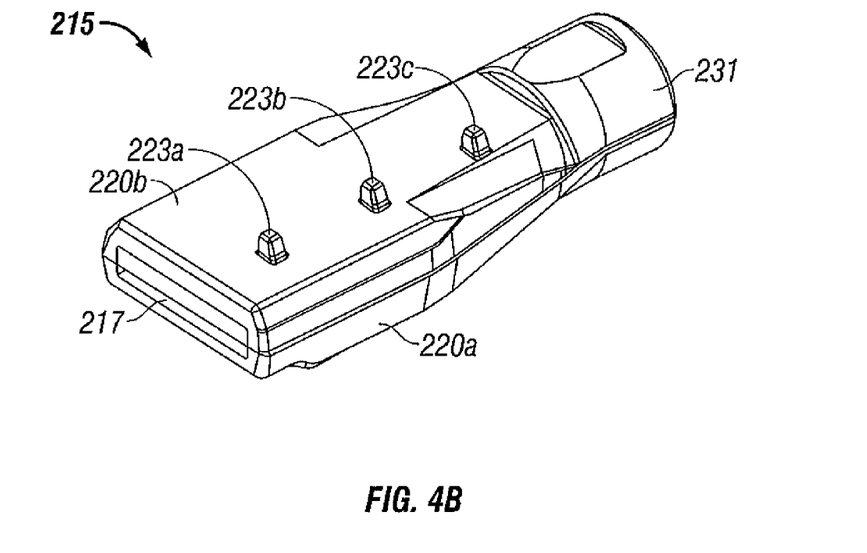
FIG. 4B is an assembled, bottom perspective view of the fluid seal of FIG. 3.

An outer surface of housing half section 220a includes at least one upper support member 221 formed proximal a distal end thereof that engages an inner surface of housing half section 220a. An outer surface of housing half section 220b includes one or more lower support members 223a-223c formed along the length thereof that contact and engage an inner surface of housing half section 220b. Upper support member 221 and outer support members 223a-223c function in concert to secure and reduce free-play in fitting of housing 220 into housing 102 during assembly. Additionally, upper support member 221 and lower support members 223a-223c function to engage an inner surface of housing 102 such that, upon assembly of housing 102, support members 221 and 223a-223c compress housing 220 to enhance the fluid-tight seal between housing 220, VDN 127 and connecting wire 224.

Referring now to FIG. 3, an exploded view of housing 220 is shown illustrating one configuration of a seal member 225 between housing half sections 220a and 220b. More specifically, sealing member 225 is supported between housing half section 220a and 220b to prevent the ingress of fluids and contaminants into housing 220.

Proximal end 227b of housing half section 220b includes a semi-circular shaped flange 231b configured to matingly receive a semi-circularly shaped lower wire support 260b therein. A pair of apertures 271a, 271b are defined within a pair of opposing faces 275a, 275b, respectively, of flange 231b and extend at least partially therethrough. Apertures 271a, 271b are configured to engage (e.g., in a snap-fit manner) a pair of corresponding lower retention posts 273a, 273b that extend from lower wire support 260b, such that lower wire support 260b complements the inner profile of flange 231b.

A distal end of housing half section 220b includes a slot 217 (FIG. 2) formed in an inner surface thereof defined upon assembly by slot halves 217a and 217b of housing half sections 220a and 220b, respectively. Slot 217 is configured to receive the proximal end of VDN 127. A circuit seal 240 is disposed within slot 217 and includes a seal portion 240a and a retaining portion 240b. A retaining recess 241 is defined in slot half 217b and is configured to matingly engage retaining portion 240b (e.g., in a snap-fit manner) therein, such that seal portion 240a complements the inner profile of slot half 217b. Upon assembly of housing 220, seal portion 240a is configured to engage the surface of VDN 127 in a fluid-tight, seal-fit manner, as will be discussed in further detail below.

Similar to housing half section 220b, a proximal end 227a of housing half section 220a includes a semi-circularly shaped flange 231a, configured to matingly receive a semi-circularly shaped wire seal support 260a therein. A retaining recess 265 (shown in phantom) is formed in an inner surface of outer surface half section 231a. Retaining recess 265 is configured to engage (e.g., in a snap-fit manner) an upper retention member 261 formed on upper wire seal support 260a, such that upper wire seal support 260a complements the inner profile of flange 231a. Upon formation of housing 220, upper wire seal support 260a substantially aligns with lower wire seal support 260b to form a circumferential seal around connecting wire 224. More particularly, upper and lower wire seal supports 260a and 260b include mutually engaging opposing sections that encapsulate and secure connecting wire 224 upon assembly of housing 220. In this manner, the ingress of fluids and contaminants is prevented at the proximal connection point of the connecting wire 224 into housing 220.

A distal end of housing half section 220a includes a slot half 217a formed in an inner surface thereof that complements slot half 217b. Slot half 217a is disposed between the outer periphery of housing half section 220a and is configured to receive a distal end 250 of seal member 225 therein. Distal end 250 includes a circuit recess 250a defined therein and an upper retaining portion 250b. A distal retaining recess 251 (shown in phantom) is formed proximal slot half 217a and is configured to engage (e.g., in a snap-fit manner) upper retaining portion 250b therein, such that distal end portion 250 complements the inner profile of slot half 217a. Circuit recess 250a is configured such that, upon formation of housing 220, circuit recess 250a substantially aligns with seal portion 240a of circuit seal 240 to form distal slot 217 for engaging VDN 127. Upon assembly of housing 220, VDN 127 is sandwiched between seal 240 and the distal end 250 of seal 225 to form a fluid-tight seal at a distal end of housing 220.

As shown in FIG. 3, seal member 225 is configured to complement the peripheral profile of housing 220. Specifically, housing half sections 220a and 220b include respective peripheral grooves 227a (obstructed view) and 227b formed therein for accommodating seal member 225 between housing half sections 220a and 220b upon formation of housing 220. To accomplish this purpose, seal member 225 is typically made from a rubber material such as silicone, urethane, perfluoro-elastomer, nitrite rubber, nitrite hydride rubber (H—NBR), fluoro rubber, acrylic rubber, styrene rubber, ethylene propylene rubber, or the like. In embodiments, each of housing half sections 220a and 220b and seal member 225 may be separately formed by injection molding a plastic material (e.g., thermoplastic elastomer).

In the embodiment of FIG. 3, housing 220 is formed by positioning seal member 225 within peripheral grooves 227a and 227b and mechanically engaging housing half sections 220a and 220b to one other. Housing half sections 220a and 220b may be coupled together using known methods, e.g., sonic energy, welding, overmolding, adhesives, snap-fit assemblies, etc. In this manner, seal member 225 is compressed between housing half sections 220a and 220b and provides a fluid-tight seal for the inner circuitry of VDN 127 and electrical contacts (not shown) associated therewith. Seal member 225 may also be bonded to one or both housing half sections 220a and 220b via a suitable adhesive prior to the housing half sections 220a and 220b being coupled together.

In another embodiment, housing 220 may be formed by multi-component molding (e.g., a two-shot injection molding) a plastic material (e.g., thermoplastic elastomer). Multi-component molding may include techniques such as, for example, two-shot molding, co-injection molding, hard-soft combinations of thermoplastics, and the like. Multi-component molding may be used to design components in arrays to reduce assembly labor and eliminate defects caused by improper orientation typical with individual components.

In this embodiment, seal member 225, circuit seal 240, lower wire seal support 260b, and housing half sections 220a and 220b are formed through a multi-step molding process that produces housing 220 as an assembly. For example, housing half sections 220a and 220b may be formed by injecting a plastic material into a first mold tool (not shown). Once hardened, housing half sections 220a and 220b are removed from the first mold and placed in a second mold tool (not shown) such that the inner surfaces of housing half sections 220a and 220b are exposed. Silicone is injected to at least partially encapsulate slot 217b and flange 231b to form circuit seal 240 and lower wire seal support 260b, respectively. Further, silicone is injected to at least partially encapsulate slot half 217a, flange 231a, and periphery groove 227a to form seal member 225. In this manner, proper orientation of seal member 225, circuit seal 240, and lower wire seal support 260b relative to housing 220 is ensured. Once formed, housing half sections 220a and 220b may be coupled using known methods. In this manner, seal member 225, circuit seal 240, and lower wire seal support 260b are all compressed between housing half sections 220a and 220b in proper orientation on assembly.

Housing half section 220b also includes one or more inner support members 230a-230d formed along an inner surface thereof. VDN 127 extends through slot 217 at least partially into housing 220 to contact inner support members 230a and 230b. In this manner, inner support members 230a and 230b are configured and positioned to prevent further proximal movement of VDN 127 within housing. Inner support members 230c and 230d are arranged to provide a guide path for connecting wire 224, such that connecting wire 224 extends between inner support members 230c and 230d to electrically connect to the proximal end of VDN 127. Electrical connection of VDN 127 to the proximal end of VDN 127 may be achieved through use of solder joints, crimps, or the like. Housing half section 220a may also include one or more inner support members (not explicitly shown) that complement inner support members 230a-230d to further support VDN 127 within housing 220.

Figure 5:
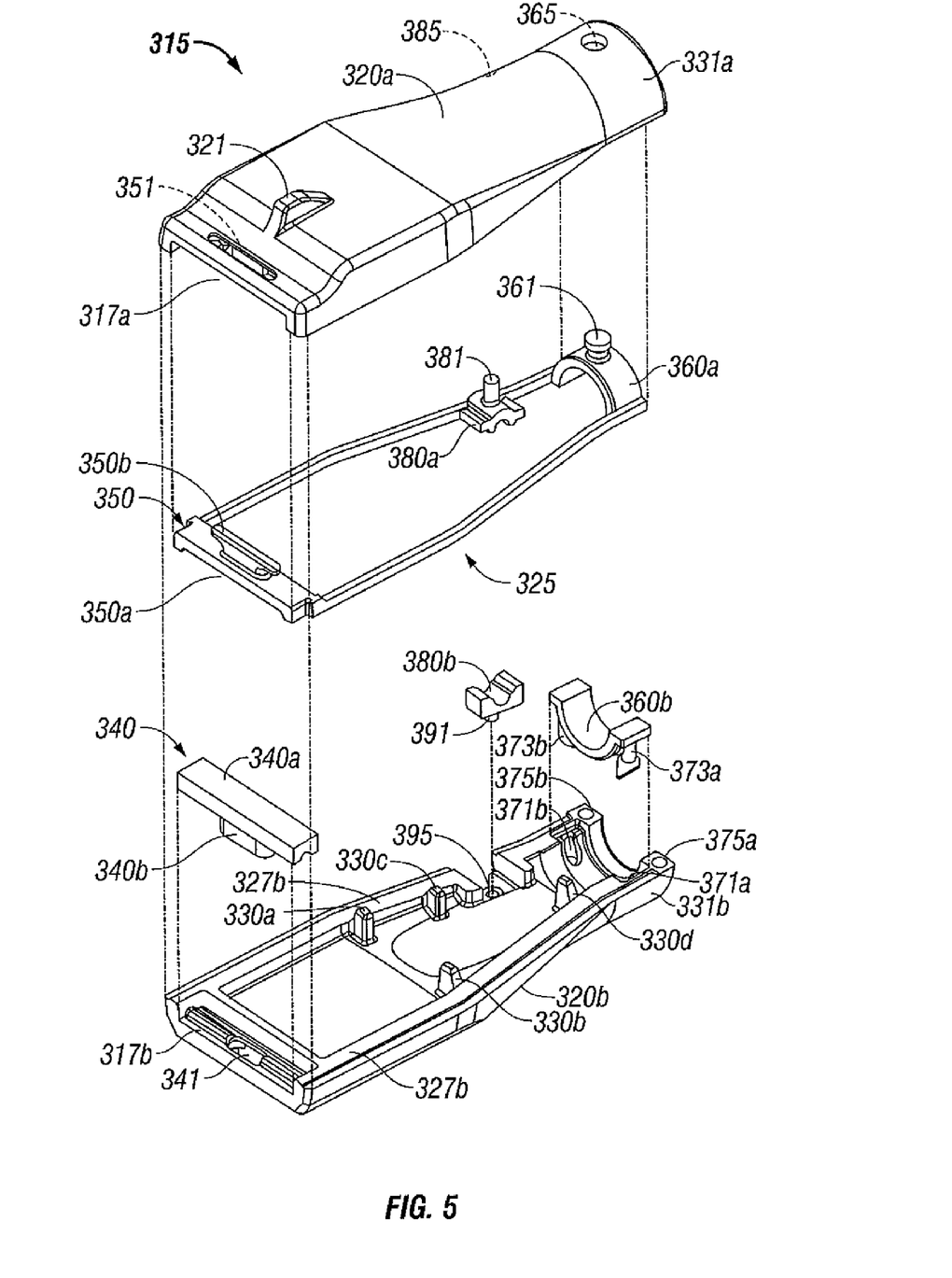
FIG. 5 is an exploded, perspective view of a fluid seal in accordance with another embodiment of the present disclosure.
Figure 6A:
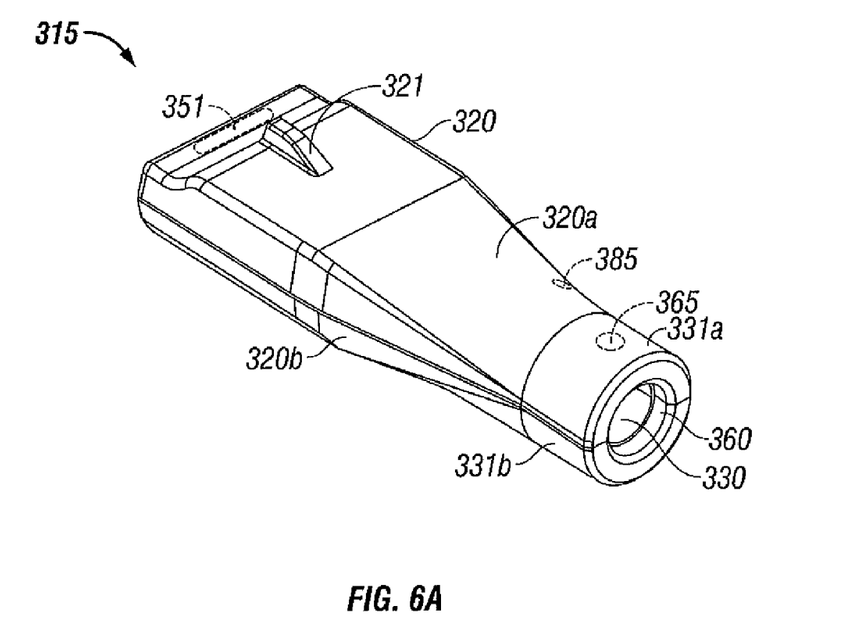
FIG. 6A is an assembled, top perspective view of the fluid seal of FIG. 5.
Figure 6B:
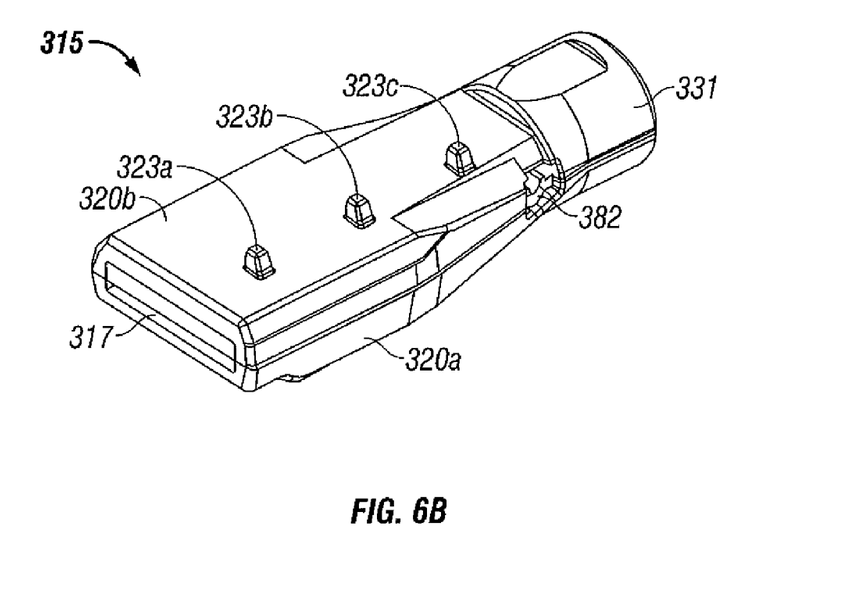
FIG. 6B is an assembled, bottom perspective view of the fluid seal of FIG. 5.

Referring now to FIGS. 5, 6A, and 6B, another embodiment of a fluid resistant seal connector 315 is shown. Fluid resistant seal connector 315 is constructed similarly to fluid resistant seal connector 215 of FIGS. 2, 3, 4A, and 4B and is only described to the extent necessary to illustrate the differences with respect to the prior described seal 215.

In addition to a proximal opening 330, through which a connecting wire 224 (FIG. 2) is introduced, and a distal slot 317, through which the VDN 127 (FIG. 2) is configured to electrically connect to connecting wire 224, fluid resistant seal connector 315 includes a side port 382 defined in housing 220, configured to accommodate an additional wire or cable (not explicitly shown) independent from connecting wire 224. Additional wires may include, but are not limited to, a radio-frequency wire, a control wire, and/or a power supplying wire. In this scenario, electrosurgical pencil 100 may include an additional opening defined in housing 102 (not explicitly shown) that substantially aligns with side port 382 of fluid resistant seal connector 315 upon placement within housing 102 of electrosurgical pencil 100.

Referring now to FIGS. 5 and 6B specifically, an inner surface of half sections 320a and 320b include side port 382 defined along respective peripheries thereof, such that, upon formation of housing 320, side port 382 is accessible between a proximal and distal ends of housing 320. Side port 382 is configured to receive a generally semi-circularly shaped wire seal 380 therein having halves 380a and 380b. Wire seal half 380b includes a wire seal retention member 391 formed thereon that is engageable with a corresponding recess 395 formed in side port 382 (e.g., in a snap-fit manner).

Wire seal portion 380a includes an upper retention member 381 formed along a periphery of seal member 325 such that, upon assembly of housing 320, wire seal portions 380a and 380b substantially align and mutually oppose one another to form generally circular side port 382. More particularly, wire seal portions 380a and 380b include mutually engaging opposing sections that encapsulate and secure a wire or cable upon assembly of housing 320. An inner surface of housing half section 320a includes a retention recess 385 (shown in phantom) formed therein configured to receive (e.g., in a snap-fit manner) upper retention member 381.

The positioning of side port 382 through housing 320 shown in FIGS. 5 and 6B is illustrative only in that housing 320 may be formed to define one or more side polls 382 along either side of housing 320. In embodiments, housing 320 may be formed to define additional openings (not explicitly shown) to accommodate various wires or cables extending therethrough for connection to VDN 127 and/or connecting wire 224.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A fluid resistant seal connector for an electrosurgical handpiece, comprising:
a housing adapted to be supported within an electrosurgical handpiece, the housing including opposing half sections each having a peripheral groove formed therein; and
a first seal adapted to engage an activation circuit of the handpiece and at least one second seal adapted to engage an electrosurgical supply wire in a fluid-tight relationship therewith, at least one of the first and second seals configured to complement the peripheral grooves formed in the housing.

2. An electrosurgical handpiece according to claim 1, wherein the housing is formed of a first material and the seals are formed of a second material.

3. An electrosurgical handpiece according to claim 1, wherein the housing half sections are formed via an injection molding process.

4. An electrosurgical handpiece according to claim 1, wherein the first seal includes mutually engaging opposing sections that engage and encapsulate a portion of the activation circuit upon assembly of the housing.

5. An electrosurgical handpiece according to claim 1, wherein the second seal includes mutually engaging opposing sections that engage and encapsulate a portion of the activation circuit upon assembly of the housing.

6. An electrosurgical handpiece according to claim 1, wherein the activation circuit is a voltage divider network.

7. An electrosurgical handpiece according to claim 1, wherein the housing includes a plurality of support members disposed on an inner surface thereof, the plurality of support members configured to support an electrical connection between the supply wire and the activation circuit.

8. An electrosurgical handpiece according to claim 1, wherein the housing includes a plurality of support members disposed on an outer surface thereof, the plurality of support members configured to support and secure the housing within the electrosurgical handpiece.

9. An electrosurgical handpiece according to claim 1, wherein the housing half sections are coupled together utilizing at least one of an adhesive, a fastener, a welding process, and sonic energy.

10. A fluid resistant seal connector for an electrosurgical handpiece, comprising:
a housing adapted to be supported within an electrosurgical handpiece, the housing including opposing half sections each having a peripheral groove formed therein;
a first seal adapted to engage an activation circuit of the handpiece and at least one second seal adapted to engage an electrosurgical supply wire in a fluid-tight relationship therewith, at least one of the first and second seals configured to complement the peripheral grooves formed in the housing, the seals including mutually engaging opposing sections that encapsulate and secure the respective activation circuit and supply wire upon assembly with the opposing half sections of the housing; and
a plurality of support members disposed on the outer periphery of the housing configured to engage an inner surface of the electrosurgical handpiece wherein upon assembly of the handpiece, the support members compress the housing to enhance the fluid-tight seal between the housing, activation circuit and support wire.

11. A method of manufacturing a fluid seal connector for an electrosurgical handpiece, comprising:
providing: a housing adapted to be supported within an electrosurgical handpiece, the housing including opposing half sections each having a peripheral groove formed therein; and
a first seal and at least one second seal configured to complement the peripheral grooves formed in the housing;
engaging the first seal with an activation circuit;
engaging the second seal with an electrosurgical supply wire; and
assembling the housing such that the first and second seals encapsulate the respective activation circuit and supply wire in a fluid-tight manner.

12. A method according to claim 11, wherein the housing of the providing step further includes a plurality of support members disposed on an outer periphery thereof and configured to engage an inner surface of the electrosurgical handpiece, wherein upon assembly of the handpiece, the support members compress the housing to enhance the fluid-tight seal between the housing, activation circuit and support wire.

13. A method according to claim 11, wherein the providing step further comprises forming the housing half sections via an injection molding process.

14. A method according to claim 11, further comprising providing a plurality of support members disposed on an inner surface of the housing configured to support an electrical connection between the supply wire and the activation circuit.

15. A method according to claim 11, further comprising forming the housing and the seals as an assembly via a two-shot injection molding process.

16. A method according to claim 11, further comprising coupling the housing half sections together utilizing at least one of an adhesive, a fastener, a welding process, and sonic energy.

17. A method according to claim 11, wherein the activation circuit of the engaging the first seal step is a voltage divider network.

18. A method according to claim 11, wherein the first seal of the providing step includes mutually engaging opposing sections that engage and encapsulate a portion of the activation circuit upon assembly of the housing.

19. A method according to claim 11, wherein the second seal of the providing step includes mutually engaging opposing sections that engage and encapsulate a portion of the activation circuit upon assembly of the housing.

20. A method according to claim 11, further comprising forming the housing of a first material and forming the seals of a second material.

* * * * *